United States Patent
Munk et al.

(10) Patent No.: US 8,202,562 B2
(45) Date of Patent: Jun. 19, 2012

(54) IMMUNOGLOBULIN AND FATTY ACIDS

(75) Inventors: Jens Kristian Munk, Hedehusene (DK); Gunner Jacobsen, Blommenslyst (DK); Karl Jørgen Jensen, Vejle (DK); Frank Bønløkke Andersen, Rødekro (DK)

(73) Assignee: Biofiber-Damino A/S, Gesten (DK)

( * ) Notice: Subject to any disclaimer, the term of this patent is extended or adjusted under 35 U.S.C. 154(b) by 845 days.

(21) Appl. No.: 12/065,770

(22) PCT Filed: Sep. 8, 2006

(86) PCT No.: PCT/DK2006/050040
§ 371 (c)(1),
(2), (4) Date: Nov. 25, 2008

(87) PCT Pub. No.: WO2007/054103
PCT Pub. Date: May 18, 2007

(65) Prior Publication Data
US 2009/0148564 A1    Jun. 11, 2009

Related U.S. Application Data

(60) Provisional application No. 60/715,187, filed on Sep. 9, 2005.

(30) Foreign Application Priority Data
Sep. 9, 2005 (DK) ................................. 2005 01263

(51) Int. Cl.
*A23K 1/18* (2006.01)

(52) U.S. Cl. ........ 426/601; 426/613; 426/805; 426/807; 426/2

(58) Field of Classification Search ................. 426/601, 426/805, 2, 613, 807
See application file for complete search history.

(56) References Cited

U.S. PATENT DOCUMENTS

| | | | |
|---|---|---|---|
| 4,096,244 A | 6/1978 | Newson | |
| 5,102,656 A | 4/1992 | Kasat | |
| 5,143,718 A | 9/1992 | Bar-Shalom | |
| 5,198,416 A | 3/1993 | Hale et al. | |
| 5,686,490 A * | 11/1997 | Okazaki et al. | 514/558 |
| 5,788,956 A | 8/1998 | De Lacharriere et al. | |
| 5,795,602 A * | 8/1998 | Craig et al. | 426/2 |
| 6,271,295 B1 | 8/2001 | Powell et al. | |
| 6,541,047 B1 * | 4/2003 | Claycamp et al. | 426/2 |

FOREIGN PATENT DOCUMENTS

| | | |
|---|---|---|
| DE | 196 31 792 A1 | 8/1996 |
| DE | 196 43 063 A1 | 10/1996 |
| EP | 0 386 018 B1 | 9/1990 |
| EP | 0 875 235 B1 | 12/2003 |
| JP | 63-119655 | 5/1988 |
| JP | 63222659 A * | 9/1988 |
| JP | 08289734 A * | 11/1996 |
| JP | 2000-017174 | 1/2000 |

OTHER PUBLICATIONS

Aumaitre et al. (Ann. Rech. Vet., 1978, vol. 9(2), pp. 181-192.*
Baldwin et al. (Journal of Biological Chemistry, vol. 155, pp. 407-412, Oct. 1944).*
Gorban et al. (Int. J Food Sci & Nutr., 2001, vol. 52, pp. 283-287).*
Patent Abstracts of Japan vol. 2003, No. 12, Dec. 5, 2003, JP 2005 013894 (Hakuto Co., Ltd.).
J. Csapo et al., "Protein, Fats, Vitamin and Mineral Concentrations in Porcine Colostrum and Milk from Parturition to 60 Days", Int. Dairy Journal 6 (1996) 881-902.
F. Klobasa et al., "Composition of Sow Milk During Lactation", J. Anim. Sci. 1987, 64: 1458-1466.
J.E. Butler, "Bovine Immunoglobulins: An Augmented Review", Veterinary Immunology and Immunopathology, 4(1983) 43-152.
XP-002407108—CN20011004310, Artificial Colostrum, Beijing Yangyuan Veterinary Medicine Co.—Abstract, Sep. 2002.
C.O. Leskanich et al., "The comparative roles of polyunsaturated fatty acids in pig neonatal development", British Journal of Nutrition (1999) 81, 87-106.
G.G. Gomez et al., "Effect of Immunoglobulin Source on Survival, Growth, and Hematological and Immunological Variables in Pigs", J. Anim. Sci. 1998, 76:1-7.
Belitz, Grosch: "Food Chemistry", 1999, p. 474.
Cosmetics, Jan. 18, 2001, pp. 509-515.
Notice of Reasons for Rejection Japanese Patent Application No. 2008-547856 dated Aug. 9, 2011.

* cited by examiner

*Primary Examiner* — Chhaya Sayala
(74) *Attorney, Agent, or Firm* — Stephen A. Bent; Foley & Lardner LLP

(57) ABSTRACT

The present invention relates to a composition comprising 0.1-10 w/w % immunoglobulin (Ig), 4-14 w/w % saturated fatty acids, 4-14 w/w % mono-unsaturated fatty acids and 0-5 w/w % poly-unsaturated fatty acids, wherein the weight percentages are based on the content of dry matter in the composition. In particular it relates to the use of said composition as a feed and/or a food composition.

8 Claims, No Drawings

IMMUNOGLOBULIN AND FATTY ACIDS

FIELD OF THE INVENTION

The present invention relates to a composition comprising 0.1-10 w/w % immunoglobulin (Ig), 4-14 w/w % saturated fatty acids, 4-14 w/w % mono-unsaturated fatty acids and 0-5 w/w % poly-unsaturated fatty acids, wherein the weight percentages are based on the content of dry matter in the composition. In particular it relates to the use of said composition as a feed and/or a food composition.

BACKGROUND ART

In piglet rearing, several problems may and do occur. One is the lack of enough teats to accommodate the entire litter; a second is the fact that the milk quality differs markedly between teats, the front teats having a better quality. The litter quickly establishes an internal hierarchy leaving the lower-quality sow's milk to the weaker piglets. This can be detrimental to weak piglets, resulting in high piglet mortality.

Farmers have sought many solutions to aiding the weaker piglets including the use of a nursing sow.

However, it is usually not all the piglets which survive even if they have been transferred to a nursing sow. This may be due to the fact that it is not always for practical reasons to move the piglets to the nursing sow soon after birth or maybe the inability of the newborn piglet to fight the other piglets for a teat affects the piglet psychologically.

The importance of antibodies in the diet given to newborn piglets is well known, see e.g. Gomez GG, (1998), J. Anim. Sci, 76, 1-7.

Leskanich C O and Noble R C, (1999), British Journal of Nutrition, 81, 87-106 discloses the comparative roles of poly-unsaturated fatty acids in pig neonatal development.

Klobasa F et al., (1987), J Anim Sci, 64(5), 1458-66 discloses the composition of sow milk during lactation.

Csapó, J-M et al., (1996), International Dairy Journal, 6, 881-902 discloses protein, fats, vitamin and mineral concentrations in porcine colostrum and milk from parturition to 60 days.

For commercial farming the price of such solutions generally needs to be rather low because it affects the profit margin of the pig. Thus there is a constant need for compositions which are suitable as feed and/or fodder compositions.

SUMMARY OF THE INVENTION

In a first aspect the present invention relates to a composition comprising 0.1-10 w/w % Ig, 4-14 w/w % saturated fatty acids, 4-14 w/w % mono-unsaturated fatty acids and 0-5 w/w % poly-unsaturated fatty acids, wherein the weight percentages are based on the content of dry matter in the composition.

The present invention also relates to a method of preparing said composition, and the use of this composition.

DETAILED DESCRIPTION

Definitions

In the context of the present invention the reference to "w/w %" is to be, unless otherwise stated, calculated on the basis of the content of solids, i.e. as the weight/weight percentage of the content of dry matter. In this context the term "dry matter" refers to the solids in a composition which are present after evaporation of any free water.

In some instances there may be referred to a composition comprising one or more components, wherein the sum of said components is less than 100 w/w %. This means that the composition may comprise other components than those specified in that particular context.

Immunoglobulins

The present invention relates to a composition comprising 0.1-10 w/w % Ig, 4-14 w/w % saturated fatty acids, 4-14 w/w % mono-unsaturated fatty acids and 0-5 w/w % poly-unsaturated fatty acids, wherein the weight percentages are based on the content of dry matter in the composition.

The inventors of the present invention have discovered that besides immunoglobulins, in particular Ig, the amount of the different groups of fatty acids are also important, for e.g. newborn piglets.

When a fodder composition for animals, such as newborn animals, e.g. newborn piglets, is prepared colostrum is often used as a source of immunoglobulins. Colostrum is the milk that is secreted during the first few days after parturition.

The composition of porcine colostrum appears to be "optimised" for the newborn piglet with regard to both the content of immunoglobulins and the amount of the different fatty acids. However, porcine colostrum is not commercially readily available (except for the use of nursing sows) thus it is difficult to use this to feed newborn piglets, at least on an industrial basis. Furthermore, those piglets, which are not able to fight the other piglets for a teat, will not obtain any colostrum from their mother and it would therefore be an advantage to be able to feed them with a composition which comprises the necessary components and which is feasible to produce on an industrial scale. In contrast to porcine colostrum, colostrum from other animals such as cows, goats, camels, sheep etc. is more readily available.

It has been shown that bovine antibodies are 80% effective in piglets (Harada et al, 2002 J Vet Med A. 49 (7): 358-364). However, the content of the different fatty acids in e.g. bovine colostrum is different from that found in porcine colostrum. For example the content of mono- and poly-unsaturated fatty acids is lower in bovine colostrum than in porcine colostrum. Furthermore, bovine colostrum is a rather expensive ingredient and it would therefore be an advantage if part of the bovine colostrum given to a newborn piglet could be substituted with other ingredients, in particular ingredients which are cheaper.

Without being bound by any theory the inventors of the present invention believe that the combination of Ig with the saturated and mono- and poly-unsaturated fatty acids according to the present invention is adequate to support the survival of newborn piglets, in particular those which are not able to fight the other piglets for a teat.

The composition of the present invention comprises in the range of 0.1-10 w/w % Ig, such as in the range of 1-10 w/w %, or in the range of 1-5 w/w %, or in the range of 1-4 w/w %, or in the range of 1-3 w/w %, or in the range of 2-9 w/w %, or in the range of 2-8 w/w % or in the range of 2-7 w/w %, or in the range 2-6 w/w %, or in the range of 2-5 w/w %, or in the range of 2-4 w/w %, or in the range of 2.5-5 w/w %, or in the range of 2.5-4.5 w/w %, or in the range of 2.5-4 w/w %.

In principle any source of Ig may be used in the composition. The Ig may in one embodiment be IgG, IgA or IgM, most particularly IgG. The Ig may also be IgY which is found in poultry. The Ig may in one embodiment derive from cow, goat, sheep, pig, poultry or camel.

In one embodiment colostrum, with the proviso that it is not porcine colostrum, may be used as a source of Ig. Thus the Ig of the present invention may be obtained from colostrum with the proviso that it is not porcine colostrum. The colostrum may be from a cow, goat, sheep or camel, in particular the colostrum may be from a cow.

Colostrum is generally recognised as being the milk secreted for the first few days after parturition and it is characterized by a high protein (other proteins than antibodies) and antibody content. In the context of the present invention colostrum is to be understood as the milk which is secreted for the first few days after parturition and which comprises at least 5 w/w % Ig (immunoglobulin). In particular the colostrum may comprise at least 6 w/w % Ig, such as at least 7.5 w/w % Ig, or at least 10 w/w % Ig, or at least 12.5 w/w % Ig, or at least 15 w/w % Ig, or at least 17.5 w/w % Ig, or at least 20 w/w % Ig, or at least 25 w/w % Ig, or at least 30 w/w % Ig, or at least 35 w/w % Ig, or at least 40 w/w % Ig, or at least 45 w/w % Ig. Defatted colostrum generally comprises a maximum of 50 w/w % Ig, while so-called whole colostrum has been found to comprise a maximum of 35 w/w % Ig.

Thus the maximum content of Ig in colostrum depends on the type of colostrum and it may be between any of the above-mentioned minimum and maximum limits.

Thus the composition of the present invention may in one embodiment comprise colostrum, with the proviso that said colostrum is not porcine colostrum.

The amount of colostrum which it is necessary to include in the composition to obtain an Ig level of between 0.1-10 w/w % depends on the type and/or quality of the colostrum used. However, it is possible for a person skilled in the art to adjust this to obtain the necessary amount.

Colostrum may be obtained by milking an animal or human being within the first few days after parturition. As the content of antibodies in the colostrum rapidly decreases as a function of time (starting from parturition) it is an advantage to use colostrum which is produced within the first 5 days after parturition, such as in particular 4, 3, 2 or 1 day(s) or shortly after parturition. The choice of animal species from where the colostrum is obtained, the time of the year, the diet of the animal and other factors may affect the amount of Ig which is present in the colostrum.

In one embodiment the colostrum may be obtained from the first and/or second milkings after parturition. The colostrum may be so-called whole colostrum, i.e. it may be colostrum which is obtained directly from the milking without removing any components. The colostrum may be obtained by spray-drying the colostrum obtained from the first and/or second milkings of the animal or human, wherein said animal may be one of the above mentioned animals, such as a cow.

However, in another embodiment the colostrum may be produced by removal of one or more components of the colostrum. For example in one embodiment the colostrum may be defatted, which means that at least a part of (such as more than 50 w/w %, or more than 60 w/w %, or more than 70 w/w %, or more than 80 w/w %, or more than 90 w/w %) of the fat has been removed. Methods for removing fat from milk or colostrum are well known to a person skilled in the art, e.g. it may for example be done by centrifugation of the milk or colostrum.

In another embodiment colostrum from which casein has been removed or at least a part of the casein (such as more than 50 w/w %, or more than 60 w/w %, or more than 70 w/w %, or more than 80 w/w %, or more than 90 w/w %) has been removed, may be used in the composition of the present invention. Casein is a protein which is present in milk (and colostrum) and it may be removed from milk (and colostrum) by precipitation with acid and/or rennin, i.e. casein will be present in the precipitate and then colostrum without this precipitate may be used in the composition of the present invention.

Colostrum from which both fat and casein has been removed may also be used in the present invention, such defatted and "casein-free" colostrum (or other types of milk) is generally known as whey.

The composition may in one embodiment comprise in the range of 15-100 w/w % colostrum, with the proviso that the colostrum is not porcine colostrum. For example, the content of colostrum may be in the range of 20-90 w/w %, such as between 20-80 w/w %, or between 30-80 w/w %, or between 30-60 w/w %, or between 35-55 w/w % or between 40-55 w/w %.

Colostrum generally comprises fatty acids, however the ratio between saturated, mono-unsaturated and poly-unsaturated fatty acids is different in for example bovine colostrum vs. porcine colostrum. Thus the present invention relates to a composition wherein colostrum, with the proviso that the colostrum is not porcine colostrum, has been mixed with fatty acids so that the ratio between saturated, mono-unsaturated and poly-unsaturated fatty acids in the composition is similar to the ratio between these fatty acids in porcine colostrum.

As also described above it is foreseen that other sources of Ig may be used. Another good source of Ig is plasma, thus in another embodiment the Ig may be obtained from plasma, such as porcine plasma.

Another source of Ig which may be used in the present composition is Ig which is obtained from poultry.

Thus in one embodiment of the present invention the Ig is obtained from one or more of these animals. The Ig may in particular be bovine Ig.

Fatty Acids

In chemistry, especially biochemistry, a fatty acid is a carboxylic acid (or organic acid), often with a long aliphatic tail (long chains), either saturated or unsaturated. Most of the natural fatty acids have an even number of carbon atoms, because they are made up by continuously elongating even-numbered carboxylic acids with acetate which has two carbon atoms.

Fatty acids may exist as "free" fatty acids, however, natural occurring fatty acids are generally found as parts of a triacylglyceride, which is a triester of glycerol and three fatty acids. Triacylglycerides are also commonly referred to as triglycerides.

Although such "free" fatty acids may be used in a composition of the present invention, the fatty acids may in particular be present in the composition as a triacylglyceride because "free" fatty acids are generally more difficult to handle than triacylglycerides.

Fatty acids may be divided into three different groups; saturated fatty acids, mono-unsaturated fatty acids and poly-unsaturated fatty acids.

Saturated Fatty Acids

Saturated fatty acids are fatty acids which do not contain any double bonds or other functional groups along the chain. The term "saturated" refers to hydrogen, in that all carbons (apart from the carboxylic acid [—COOH] group) contain as many hydrogens as possible. In other words, the omega ($\omega$) end contains three hydrogens ($CH_3$—) and each carbon within the chain contains two hydrogens (—$CH_2$—). Saturated fatty acids are sometimes abbreviated SFA.

Examples of some saturated fatty acids include but are not limited to:
Butyric: $CH_3(CH_2)_2COOH$
Lauric (dodecanoic acid): $CH_3(CH_2)_{10}COOH$
Myristic (tetradecanoic acid): $CH_3(CH_2)_{12}COOH$
Palmitic (hexadecanoic acid): $CH_3(CH_2)_{14}COOH$
Stearic (octadecanoic acid): $CH_3(CH_2)_{16}COOH$
Arachidic (eicosanoic acid): $CH_3(CH_2)_{18}COOH$ Thus one or more of the above mentioned saturated fatty acids may be used in the composition of the present invention. It is also contemplated that combinations of these fatty acids may be used. The saturated fatty acids present in the composition of the present invention may comprise at least one selected from the group consisting of butyric ($CH_3(CH_2)_2COOH$), lauric acid (dodecanoic acid; $CH_3(CH_2)_{10}COOH$), myristic acid (tetradecanoic acid; $CH_3(CH_2)_{12}COOH$), palmitic acid (hexadecanoic acid; $CH_3(CH_2)_{14}COOH$), stearic acid (octadecanoic acid, $CH_3(CH_2)_{16}COOH$), arachidic acid (eicosanoic acid; $CH_3(CH_2)_{18}COOH$).

In one embodiment the saturated fatty acids of the present in the composition of the present invention are selected from the group consisting of butyric ($CH_3(CH_2)_2COOH$), lauric acid (dodecanoic acid; $CH_3(CH_2)_{10}COOH$), myristic acid (tetradecanoic acid; $CH_3(CH_2)_{12}COOH$), palmitic acid (hexadecanoic acid; $CH_3(CH_2)_{14}COOH$), stearic acid (octadecanoic acid, $CH_3(CH_2)_{16}COOH$), arachidic acid (eicosanoic acid; $CH_3(CH_2)_{18}COOH$). If colostrum, in particular colostrum from any of the above mentioned animals, i.e. cows, goats, camels, sheep etc. is used as a source of Ig in the composition of the present invention this may provide an adequate amount of saturated fatty acids, or it may at least provide part of the amount of saturated fatty acids present in the composition of the invention. Of course whether the amount is adequate depends on the amount and/or the quality of the colostrum which is used in the composition.

For example if so-called "whole colostrum" is used the amount of saturated fatty acids in the colostrum may be adequate for the composition of the present invention if said composition comprises at least 50 w/w % whole colostrum. "Whole colostrum" is to be understood as colostrum which is obtained directly from a mammal without changing its composition of the different components, e.g. the colostrum has not been defatted nor has the casein been removed. The term "whole colostrum" is intended to include colostrum which is e.g. dried or diluted into another component.

If the content of whole colostrum in the composition is below 50 w/w %, such as below 40 w/w %, or below 30 w/w %, other source(s) of saturated fatty acids may in particular be included in the composition.

The inventors of the present invention have noticed that when the content of colostrum is reduced it is an advantage to include another source of C16:0 and/or C18:0, also known as palmitic and stearic acid, respectively.

A good source of these particular fatty acids is whole eggs, such as whole egg powder which is egg prepared as a powder. Another good source of palmitic and stearic acid is egg yolk, thus in one embodiment the composition of the present invention may further comprise egg yolk, such as egg yolk powder. The eggs may for example be from chicken or turkey.

The egg white also comprises several amino acids which are an important part of a healthy diet and it may therefore be an advantage to use whole eggs in the composition of the present invention. Whole egg is in general a good source of protein and it can therefore be used to replace part of the colostrum as long as the level of Ig is kept between 0.1-10 w/w %, as colostrum besides being a source of Ig is also a good source of proteins.

Examples of commercially available whole egg powder include but are not limited to WAF Whole Egg Powder from Belovo and Egg Powder from Schaffelaarbos. Combinations of different sources of eggs and/or egg yolks and/or egg whites may also be used.

Mono-Unsaturated Fatty Acids

Mono-unsaturated fatty acids are of a similar form as the saturated fatty acids, except that one alkene functional group exist along the chain, where the alkene substitutes a singly-bonded ($—CH_2—CH_2—$) part of the chain with a doubly-bonded ($—CH=CH—$) portion (that is, a carbon double bonded to another carbon). The double bond is in most cases a cis bond. The mono-unsaturated fatty acids are sometimes abbreviated MUFA.

There are two different ways to denote where the double bond is located in the molecule. For example it may be denoted:
a) cis/trans-Delta-x or cis/trans-$\Delta$x: The double bond is located on the xth carbon, counting down from the carboxyl terminus. The cis or trans notation indicates whether the molecule is arranged in a cis or trans conformation.
b) Omega-x or $\omega$-x: A double bond is located on the xth carbon, counting down from the distal (methyl carbon) end.

Examples of mono-unsaturated fatty acids include but are not limited to:
Palmitoleic acid: $CH_3(CH2)_5CH=CH(CH_2)_7COOH$
Oleic acid: $CH_3(CH_2)_7CH=CH(CH_2)_7COOH$ Both palmitoleic and oleic acid are omega-9 fatty acids.

Thus one or more of the above mentioned mono-unsaturated fatty acids may be used in the composition of the present invention. It is also contemplated that combinations of these fatty acids may be used. The mono-unsaturated fatty acids present in the composition of the present invention may comprise at least one selected from the group consisting of palmitoleic acid ($CH_3(CH_2)_5CH=CH(CH_2)_7COOH$) and oleic acid ($CH_3(CH_2)_7CH=CH(CH_2)_7COOH$).

In one embodiment the mono-unsaturated fatty acids present in the composition of the present invention are selected from the group consisting of palmitoleic acid ($CH_3(CH_2)_5CH=CH(CH_2)_7COOH$) and oleic acid ($CH_3(CH_2)_7CH=CH(CH_2)_7COOH$). As for saturated fatty acids the use of colostrum in the composition of the present invention may provide part of the mono-unsaturated fatty acids of the composition. However, the amount of mono-unsaturated fatty acids in e.g. bovine colostrum is lower than the amount of such fatty acids in a composition according to the present invention. Thus if colostrum is used as a source of Ig in a composition of the present invention it may be combined with other sources of mono-unsaturated fatty acids.

In one embodiment such a mono-unsaturated fatty acid may be C18:1$\omega$9 also known as oleic acid.

As described in the section on poly-unsaturated fatty acids many different plant oils comprise mono-unsaturated fatty acid. Thus it is contemplated that one or more of these plant oils may be used as a source of mono-unsaturated fatty acids for the composition of the present invention.

Poly-Unsaturated Fatty Acids

Linolenic, docosahexaenoic, and eicosapentaenoic acids are examples of omega-3 fatty acids. Linoleic acid and arachidonic acid are omega-6 fatty acids. Stearic and oleic acid are both 18 C fatty acids. They differ only in that stearic acid is saturated with hydrogen, while oleic acid is an unsaturated fatty acid with two fewer hydrogens.

In the case of a molecule having more than one double bond, the notation is, for example, cis,cis-$\Delta$9,$\Delta$12.
(alpha)-Linolenic Acid: $CH_3(CH_2CH=CH)_3(CH2)_7COOH$ (C18:3$\omega$3)
Linoleic Acid: $CH_3(CH_2)_3(CH_2CH=CH)_2(CH_2)_7COOH$ (C18:2$\omega$6)
Arachidonic Acid: $CH_3(CH_2)_3(CH_2CH=CH)_4(CH_2)_3COOH$ (C20:4$\omega$6)

Docosahexaenoic Acid: $CH_3(CH_2CH=CH)_6(CH_2)_2COOH$ (C22:6ω3)

Eicosapentaenoic acid: $CH_3(CH_2CH=CH)_5(CH_2)_3COOH$ (C20:5ω3)

Thus one or more of the above mentioned poly-unsaturated fatty acids may be used in the composition of the present invention. It is also contemplated that combinations of these fatty acids may be used. The poly-unsaturated fatty acids present in the composition of the present invention may comprise at least one selected from the group consisting of (alpha)-linolenic acid $(CH_3(CH_2CH=CH)_3(CH2)_7COOH)$, linoleic acid $(CH_3(CH_2)_3(CH_2CH=CH)_2(CH_2)_7COOH)$, arachidonic acid $(CH_3(CH_2)_3(CH_2CH=CH)_4(CH_2)_3COOH)$, docosahexaenoic acid $(CH_3(CH_2CH=CH)_6(CH_2)_2COOH)$ and eicosapentaenoic acid $(CH_3(CH_2CH=CH)_5(CH_2)_3COOH)$.

In one embodiment the poly-unsaturated fatty acids present in the composition of the present invention are selected from the group consisting of (alpha)-linolenic acid $(CH_3(CH_2CH=CH)_3(CH2)_7COOH)$, linoleic acid $(CH_3(CH_2)_3(CH_2CH=CH)_2(CH_2)_7COOH)$, arachidonic acid $(CH_3(CH_2)_3(CH_2CH=CH)_4(CH_2)_3COOH)$, docosahexaenoic acid $(CH_3(CH_2CH=CH)_6(CH_2)_2COOH)$ and eicosapentaenoic acid $(CH_3(CH_2CH=CH)_5(CH_2)_3COOH)$.

Triglycerides or fats which have a high content of unsaturated fatty acids, are generally liquid at room temperature while triglycerides with a high content of saturated fatty acids are generally solid at room temperature.

Many vegetable oils are known to have a high content of unsaturated fatty acids. Hence if for example colostrum with the exception of porcine colostrum is used as a source of Ig in the composition of the present invention then in one embodiment a vegetable oil may be used as source of both saturated and mono- and poly-unsaturated fatty acids, in particular of mono- and poly-unsaturated fatty acids.

Porcine colostrum comprises different unsaturated fatty acids, however the main components are C18:1ω9 and C18:2ω6, thus a mono- and a poly-unsaturated fatty acid, respectively. The ratio between C18:1ω9 and C18:2ω6 in porcine colostrum is approximately 3:1 with some deviation from sow to sow and influenced by external factors. Thus the ratio between C18:1ω9 and C18:2ω6 may in one embodiment be between 6:0.5 and 1.5:2, such as between 5:0.7 and 2:1.5, or between 4:0.8 and 2:1.5, or between 3.5:0.85 and 2:1.5, or between 3.5:0.5 and 2.5:0.85, or the ratio may be approximately 3:1.

Thus sources of fatty acids which comprise such a ratio of C18:1ω9 to C18:2ω6 may in one embodiment be used in the composition of the present invention; such sources of fatty acid may in particular be used if colostrum is used as a source of Ig.

There exist a number of plants or plant-derived products which comprise a ratio of C18:1ω9 to C18:2ω6 as described above. Examples of such plants or plant-derived products include but are not limited to rape (rapeseed oil), flaxseed also known as linseed, olive, soya, maize/corn, macadamia nuts, coconut, palm, peanut, sesame, safflower, almond, apricot, babassu, cocoa, cottonseed, cupu assu, grapeseed, hazelnut, sunflower, nutmeg, poppyseed, rice bran, sheanut, teaseed, tomatoseed, ucuhuba butter, walnut, wheat germ, avocado, mustard and oat. A particular form of rape, wherein the rapeseed oil comprises a lower amount of erucic acid than normal rapeseed oil, has been bred. The oil from this particular form of rape is known as canola oil, although from a botanical point of view this is still rape. Rapeseed oil with a reduced amount of erucic acid, e.g. canola oil, may also be used in the composition of the present invention.

Thus one or more of these plant or plant-derived products may in particular be used as a source of mono- and poly-unsaturated fatty acids of the present invention. Thus it is also contemplated that the composition of the present invention comprises a combination of two or more of these plant or plant-derived products.

Other Components

Compositions, which are used as feed or food, are generally described by their protein, carbohydrate and fat content because these three groups are all of relevance for the intake of energy by an animal or human being. All of these three groups are generalised terms covering within each group structurally different proteins, including e.g. enzymes, carbohydrates and fats. Besides these groups such compositions may further comprise a number of other components which do not belong to any of these three classes or groups.

The composition of the present invention may have a content of 25-90 w/w % proteins, such as between 30-80 w/w % proteins, or between 30-70 w/w % proteins, or between 30-60 w/w % proteins, or between 40-80 w/w % proteins, or between 40-70 w/w % proteins, or between 40-60 w/w % proteins, or between 35-80 w/w % proteins, or between 35-70 w/w % proteins, or between 35-60 w/w % proteins, or between 45-55 w/w % proteins. The composition of the present invention may have a content of 5-50 w/w % fats, such as between 5-45 w/w % fats, or between 10-45 w/w % fats, or between 10-40 w/w % fats, or between 15-35 w/w % fats, or between 20-30 w/w % fats, or between 17.5-27.5 w/w % fats, or between 10-30 w/w % fats, or between 20-50 w/w % fats, or between 20-40 w/w % fats.

The composition of the present invention may have a content of 3-40 w/w % carbohydrates, such as between 5-35 w/w % carbohydrates, or between 5-30 w/w % carbohydrates, or between 5-25 w/w % carbohydrates, or between 5-20 w/w % carbohydrates, or between 5-15 w/w % carbohydrates, or between 10-35 w/w % carbohydrates, or between 10-30 w/w % carbohydrates, or between 10-20 w/w % carbohydrates, or between 10-15 w/w % carbohydrates.

In one embodiment the composition of the present invention may have a content of proteins and fats, or proteins and carbohydrates, or fats and carbohydrates, or proteins, fats and carbohydrates as described above.

The composition of the present invention may in a particular embodiment be produced by mixing components which comprise other compounds than the Ig and the different fatty acids. For example as described above colostrum may be used as a source of Ig and plant oils and/or eggs may be used as sources of fatty acids. Colostrum comprises besides Ig a range of other compounds, including proteins, fatty acids mainly in the form of triglycerides and lactose.

The choice of the particular proteins, fats and carbohydrates in the composition may vary because different components may be used to prepare the composition of the present invention.

It is not only the amount of protein in the composition, which is of relevance but also the amino acid composition may be highly relevant. If for example the composition of the present invention is to be used as a feed or food composition, such as to feed newborn piglets it may be advantageous to include sources of all amino acids, especially essential amino acids as known to a person skilled in the art, and especially sources of glutamin, glutamate, proline, methionine and phenylalanine. Examples of suitable sources of these amino acids include but are not limited to colostrum, whole egg, wheat and/or soy protein. It is also contemplated that the composition of the present invention may comprise combinations of different sources of amino acids.

In a preferred embodiment the composition of the present invention may further comprise lactose, also known as milk sugar. Lactose is a carbohydrate and it is particularly useful as a carbohydrate source for newborn piglets as it is easily metabolised in contrast to other carbohydrates which require degradation or modification by enzymes which are not yet active in the newborn piglet. Colostrum which may also be used as a source of Ig also comprises lactose. However, if for example another source of Ig than colostrum is used or if the amount of colostrum in the composition is to be reduced it may be an advantage to include another source of lactose in the composition. Whey may be used as a source of lactose. Whey is as explained above the part of the milk or colostrum which is left after centrifugation and acid and/or rennin precipitation of the milk.

The composition of the present invention may in one embodiment comprise one or more further components than Ig and the saturated and mono- and poly-unsaturated fatty acids.

Examples of such further components which may be used in the composition of the present invention include but are not limited to vitamins, antioxidants, herbs, minerals, thickeners/gums, emulsifiers, sweeteners, flavours, acids and preservatives. It is also contemplated that combinations of two or more of these components may be used in the composition of the present invention. Some compounds may have more than one function; hence these compounds may be classified in one or more of these groups.

Examples of vitamins which may be used in the composition of the present invention include but are not limited to vitamin A, vitamin B, vitamin D and vitamin E. Combinations of two or more of these vitamins may also be used in the composition of the present invention.

It may be advantageous to include antioxidants in the composition of the present invention because both mono- and poly-unsaturated fatty acids are rather unstable as they are easily oxidised by e.g. air. Many antioxidants are able to stabilise these fatty acids. Examples of suitable antioxidants which may used in the composition of the present invention include but are not limited to vitamin C and derivatives, vitamin E, salts of gallus acid, butylated hydroxyanisol (BHA), butylated hydroxytoluene (BHT), lecithin, salts of lactic acid, citric acid and its salts, tartric acid and its salts, phosphoric acid and its salts, malic acid and its salts, adipic acid and its salts, succinic acid, ethylene diamine tetraacetate (EDTA) and its salts. Combinations of two or more of these antioxidants may also be used in the composition of the present invention.

Examples of herbs which may be used in the composition of the present invention include but are not limited to oregano, in particular oregano oil, ajwain, thyme and aloe vera. Combinations of two or more of these herbs may also be used in the composition of the present invention.

Examples of suitable minerals which may be used in the composition of the present invention include but are not limited to iron, copper, manganese and zinc. These minerals are often bound in complexes and reference to the minerals is intended to include such complexes. Combinations of two or more of these minerals may also be used in the composition of the present invention.

Examples of suitable thickeners/gums which may be used in the composition of the present invention include but are not limited to guar gum, alginic acid or its salts, agar, carrageenan, philippine eucheuma seaweed, carob (locust) bean gum, traganth, gum arabic, xanthan gum, karaya gum, tara gum, gellan gum, konjac gum, pectin, cellulose, inulin and psyllium. The inclusion of a thickener in the composition of the present invention has the advantage that it increases the viscosity of the composition. This may be an advantage if the composition is to be used as a food or feed as it may improve the mouthfeel of the composition and may hinder precipitation of heavy and/or insoluble/undissolved components of the solution. Combinations of two or more of these thickeners/gums may also be used in the composition of the present invention.

It is foreseen that the composition of the present invention may be exposed to different temperatures as it may be used in different countries with different climates and also during transportation the temperature may be different than e.g. at the place where the composition is used. Thus it is an advantage if the thickener/gum has an acceptable viscosity at a temperature in the range of 0-60° C., such as in the range of 10-50° C. As the pH of the composition of the present invention in one embodiment may be in the range of e.g. 2.5-8 it is an advantage if the thickener/gum possesses an acceptable viscosity at a pH in the range of 2.5-8, such as in the range of pH 3-7, or pH 3-6, or pH 4-6, or pH 4-5, or pH 4-4.5.

Examples of emulsifiers which may suitably be used in the present invention include but are not limited to polyoxyethylene (polysorbate) and its derivatives, ammonium phosphatides, polyethylene glycol and its derivatives, beta-cyclodextrin, fatty acid salts and derivatives, mono- and diglycerides of fatty acids and derivatives thereof, propylene glycol and derivatives, polyglycerol and its derivatives, salts of lactylate, stearyl tartrate and derivatives of sorbitol. Combinations of two or more of these emulsifiers may also be used in the composition of the present invention.

A suitable example of a commercially available sweetener which is suitable for animal feed is Sucram® C-150 from Pancosma. However, it is within the scope of the present invention to use other sweeteners or combinations of sweeteners in the composition of the present invention.

A suitable example of a commercially available flavour which is suitable for animal feed is Flavodan™ CV-21514 from Danisco. However, it is within the scope of the present invention to use other sweeteners or combinations of sweeteners may be used in the composition of the present invention. In particular the composition of the present invention may also comprise a preservative so that the storage time of the composition may be prolonged. If the composition is to be used as a feed or food composition said preservative may be a preservative which is non-toxic to mammals. Furthermore, the preservative may be a preservative which protects the composition against bacterial and fungal growth for a period of at least one year. Examples of such preservatives which may be used in the composition of the present invention include but are not limited to sorbic acid and its salts, propionic acid and its salts, benzoic acid and its salts and derivatives thereof, sulphite and its salts, diphenyl, o-phenylphenol and its salts, nisin, natamycin, hexamethylenetetramine, dimethyldicarbonate, nitrite and its salts, nitrate and its salts, acetic acid and its salts, lactic acid, boric acid and its salts, carbon dioxide, malic acid, fumaric acid, calcium propionate, potassium sorbate. It is also foreseen that combinations of one or more of these compounds may be used in the composition of the present invention.

The composition of the present invention may in one embodiment have a pH in the range of 2.5-8, such as in the range of pH 3-7, or pH 3-6, or pH 4-6, or pH 4-5, or pH 4-4.5. The pH of the composition may be caused by the particular combination of different compounds in the composition, or by the method of manufacturing, e.g. if the composition is preserved by acidifying/souring or fermentation or by the addition of acidic or alkaline compounds to obtain a particular pH. Examples of suitable acids which may be included in the composition of the present invention include at least one of the acids described above, acetic acid, citric acid, phosphoric acid, hydrochloric acid, sulphuric acid or lactic acid.

As it is known that newborn piglets may encounter problems with diarrhoea it may be an advantage to include compounds which may relieve the diarrhoea. Aloe vera and oregano are believed to have such an effect and they may therefore in one embodiment be included in the composition of the present invention. Combinations of such compounds capable of relieving diarrhoea may also be included in the composition of the present invention.

Compositions of the Present Invention

As described above the composition of the present invention may in one embodiment be prepared by combining sources of Ig, saturated and mono- and polyunsaturated fatty acids, wherein one or more of these sources comprises other components. Suitable sources of Ig, saturated and mono- and poly-unsaturated fatty acids are also described above. As these components comprise different components the adjustment of the amount used of one component affects the necessary amount of another component. In one embodiment colostrum, with the exception of porcine colostrum, may be used as a source of Ig.

If for example bovine colostrum is used as a source of Ig then even with at good quality of colostrum the amount of mono- and poly-unsaturated fatty acids is lower than the amounts present in a composition according to the present invention. Furthermore, colostrum is a rather expensive component and it would therefore be an advantage to minimize the amount of colostrum in the composition. Thus in one embodiment the composition of the present invention comprises one of the combinations of components described in the following.

10-70 w/w % colostrum,
10-70 w/w % whole egg,
0.5-20 w/w % plant oil,
0.5-10 w/w % whey,
as based on the content of dry matter.

In one embodiment the sum of colostrum, whole egg powder, plant oil and whey may be 100%, i.e. the composition of the present invention may consist of these four components.

In another embodiment the composition may comprise other components than the colostrum, whole egg, plant oil and whey. Examples of such compounds or components are given below but include also those mentioned previously. In such a composition the colostrum, whole egg, plant oil and whey may comprise between 5-99.9 w/w % of the composition.

The composition may comprise a further source of proteins, which may be wheat and/or soy protein, e.g. if the composition is a feed and/or fodder composition.

The composition may further comprise components which may constitute between 0.5-20 w/w % of the composition. Examples of such further components may be any of the above mentioned and also combinations of two or more of these components may be used. The amount of the further components if present in the composition of the present invention may be:

0.1-5 w/w % vitamins,
0.01-3 w/w % herbs,
0.5-5 w/w % thickeners,
0.01-3 w/w % emulsifier,
0.5-10 w/w % preservatives,
0.01-3 w/w % antioxidants,
0.01-3 w/w % minerals,
0.04-20 w/w % acid,
0.00004-4 w/w % sweetener,
0.00004-4 w/w % flavour.

Examples of suitable colostrum, whole egg powder, plant oil, whey, vitamins, herbs, thickeners, emulsifier, preservatives, antioxidants, minerals etc. which may be used in the composition may in particular be any of the above mentioned compounds.

An example of such a suitable composition includes:
40-55 w/w %, such as 45 w/w % bovine colostrum,
40-55 w/w %, such as 44 w/w % whole egg powder,
1-4 w/w %, such as 2 w/w % whey powder,
2-8 w/w %, such as 3.4 w/w % rapeseed oil,
0.75-3 w/w %, such as 1.5 w/w % vitamin mixture,
0.25-1 w/w %, such as 0.5 w/w % emulsifier,
0.25-5 w/w %, such as 0.5 w/w % antioxidant,
1-10 w/w %, such as 2 w/w % preservative,
0.05-0.5 w/w %, such as 0.1 w/w % oregano oil,
0.5-5 w/w %, such as 0.5-2 w/w %, or 1 w/w % guar gum,
0.4-20 w/w % phosphoric acid, such as 2 w/w % phosphoric acid,
0.004-4 w/w % sweetener, such as 0.08 w/w % sweetener,
0.0004-4 w/w % flavour, such as 0.0268 w/w % flavour.

The composition of the present invention may in principle be in any form; e.g. liquid, powder, solid or gel-like form. The choice of form may depend on the components of the composition but it may also depend on the mode of administrating the composition.

Method of Preparing the Composition

The composition of the present invention may be prepared by any means. The choice of means typically depends on which sources of Ig and fatty acids are used, e.g. whether the components are powders, liquids or other forms.

If colostrum is used as a source of Ig the method of producing a composition according to the present invention may in one embodiment comprise mixing said colostrum and fatty acids.

Colostrum, which may be used in a liquid form, is often spray-dried and is therefore often used as a powder. If for example some of the oils from the above-mentioned plants are used as sources of fatty acids, these are often in a liquid form. However, for most purposes the mixing of a powder and a liquid is generally not a problem.

A factor, which may affect how thoroughly the components need to be mixed is the ratio between hydrophilic and lipophilic components in the composition as it is a well-known phenomena that these two types of components do not mix easily. Furthermore, this phenomenon of lipophilic and hydrophilic characteristics may also affect in what order it is advantageous to mix the components or compounds.

Generally manual mixing of the different components may be enough. The combination of the different components may be done by mixing water with Aloe vera gel, mix the components which are powders and add those to the water, mix the different oils (e.g. plant oil, oregano oil and/or emulsifier) separately and add them to the mixture. Mix thoroughly manually or mechanically.

If the composition of the present invention comprises colostrum, in particular as a powder, whole egg powder, whey powder, plant oil, wheat protein or soy protein these components may in one embodiment be mixed by manual mixing to obtain a powder.

This powder may then subsequently be mixed with further components, e.g. to obtain a liquid or a gel-like composition.

If Aloe vera is to be included in the composition this may be included in the above mentioned composition as a powder, e.g. as a sugar-coated powder, and/or it may be included as a gel.

If Aloe vera is to be included as a gel it may be mixed with the other components, which may form a powder, in a ratio of aloe vera to powder which may be between 0.2:1 and 1:0.2.

To increase the shelf-life of the composition of the present invention said composition may be exposed to a method of preservation.

Examples of different methods of preservation of a composition of the present invention include but are not limited to one or more of the following:
  exposing the composition to radiation,
  adding a chemical preservative,
  souring or acidifying the composition,
  adding sugar or carbohydrate,
  adding antioxidants,
  fermenting the composition by adding a microbe such as a lactic acid bacteria or yeast,
  exposing the composition to pasteurisation.

The different methods of preservation have different advantages and it is therefore also contemplated that a combination of two or more methods of preservation may be used. Typically there is a risk of contaminating a composition of the present invention with e.g. unwanted bacteria during preparation of the composition, during storage of the composition and/or during storage of a composition which is in use which means that the container comprising the composition has been opened and thereby potentially exposing the composition to contamination.

Preservation of a composition of the present invention may be performed by exposing the composition to alpha ($\alpha$), beta ($\beta$), or gamma ($\gamma$) irradiation in an amount which is able to sterilise the composition, such as 1-8 kGy gamma irradiation as e.g. described by Zeuthen P and Bøgh-Sørensen L in "Konserveringsteknink 2" (ISBN 8774325787). The length of the period of time that it is necessary to irradiate the composition depends on the effect of the source of radiation. This method is suitable to kill any bacteria which may have contaminated the composition during preparation.

Examples of chemical preservatives are given above and one or more of these may be used to preserve the composition of the present invention. The advantage of adding a chemical preservative to the composition of the present invention is that they have a long-term effect. Thus the chemical preservative may function to preserve the composition both during preparation, during storage and during storage after the composition has been taken into use.

Another method of preserving the composition is to sour or acidify the composition by adding an acid to the composition. Examples of suitable acids include but are not limited to one or more selected from the group consisting of acetic acid, citric acid, phosphoric acid, hydrochloric acid, sulphuric acid, lactic acid. The inventors of the present invention have found that by adding phosphoric acid to a composition of the present invention the composition is preserved for a longer period of time after exposure to the surroundings than when phosphoric acid is not added to the composition.

Flavours and/or sweeteners may be added to the composition of the present invention independent of whether the composition is preserved or not and independent of what method of preservation there is used. However, if the composition is preserved by souring or acidifying the composition it may be an advantage to add sweeteners and/or flavours as the inventors of the present invention have found that acetic acid gives the composition a sour flavour. However, the choice of acid may affect the taste of the composition.

Another method which it is contemplated to use to preserve a composition of the present invention is by fermenting the composition by adding one or more lactic acid bacteria. Lactic acid bacteria produce lactic acid which works as a preservative. Yeast works by converting carbohydrates into alcohol or acids, which both works as preservatives.

The presence of sugar/carbohydrates affects the water activity of the composition so that it is lowered to around 0.9 or less. As it is difficult for bacteria to live and/divide at such a low water activity the sugars/carbohydrates works as preservatives.

Use of the Composition

The composition of the present invention may in one embodiment be used as a feed or fodder.

The inventors of the present invention have found that giving newborn piglets a composition according to the present invention appears to have a beneficial effect on the survival of the newborn piglets, e.g. if it is given soon after birth to piglets which are subsequently transferred to a nursing sow. Thus the composition of the present invention may be used as a "energy-booster".

Thus in one embodiment the present invention also relates to a method of feeding a mammal, e.g. a newborn mammal, wherein said method comprises feeding a composition of the present invention to said mammal.

Examples of mammals which may be fed with a composition according to the present invention include but are not limited to at least one selected from the group consisting of farm animals, such as pigs, cows, goats, sheep, horses etc., or pets, such as dogs, cats, hamsters, etc. or to humans.

Thus even though the inventors of the present invention have found that the composition of the present invention is suitable for newborn piglets it is foreseen that it may also be suitable for other mammals.

It is generally more difficult to feed newborn mammals, as human infants than older mammals. Hence if the composition of the present invention is used to feed newborn mammals it may be an advantage to administer the composition to them with for example a syringe or a feeding bottle.

If the composition of the present invention is used to feed newborn piglets before they are transferred to a nursing sow, said piglet may e.g. be fed between 0.2-5.0 g, such as around 1.0 g, of dry-matter per feeding/portion. The composition may, as explained above, be mixed or diluted with water, thus the actual amount given to the piglet may then depend on how much the composition has been diluted. However, a person skilled in the art, e.g. a farmer is generally able to adjust this so that the piglet obtains the necessary amount of dry matter. Generally newborn piglets are not able to intake more than 50 mL per feeding/portion.

The newborn piglets are generally fed manually, e.g. with a pump or similar equipment.

The composition of the present invention may also be added to other compositions which are useful to feed animals with, such as newborn piglets. For example it may be added to a porcine or sow milk substitute composition. If the composition of the present invention is used in such a context it is foreseen that it particularly may be used to "spike" such compositions, e.g. it may constitute between 0-40 w/w % of such compositions or other compositions.

EXAMPLE

Example 1

In one application a composition comprising 45 w/w % bovine colostrum, 44 w/w % whole egg, 2 w/w % whey, 3.4 w/w % rapeseed oil, 1.5 w/w % vitamin mixture, 0.5 w/w % emulsifier, 0.5 w/w % antioxidant, 2 w/w % preservative, 0.1 w/w % oregano oil and 1 w/w % guar gum was dissolved in approximately three volumes of water to result in a product of approximately 25 w/w % dry matter. This mixture was a slightly viscous liquid and was packaged in handy bottles fitted with a pump mechanism capable of delivering approximately two ml of the mixture per pump stroke. The bottle and pump could be operated with one hand and allowed dosing to newborn piglets by holding one piglet in one hand and injecting the product directly from the pump outlet into the oral cavity of the piglet holding the bottle and pump in the other hand. The piglets then voluntarily swallowed the product without apparent discomfort. In this particular trial piglets chosen for feeding with the mixture containing the product described herein were born small and were therefore weak and a large percentage of those piglets would potentially end as fatalities. Consistent usage as soon as possible following piglet births resulted in approximate halving of fatalities amongst piglets in the farrowing pens after a few weeks of usage.

The invention claimed is:

1. A composition comprising 0.1-10 w/w % immunoglobulin (Ig), 4-14 w/w % saturated fatty acids, 4-14w/w % mono-unsaturated fatty acids and 0-5 w/w % poly-unsaturated fatty acids, wherein the weight percentages are based on the content of dry matter in the composition.

2. A composition according to claim 1, wherein the Ig derives from cow, goat, sheep, pig, poultry or camel.

3. A composition according to claim 1, wherein the Ig is obtained from colostrum with the proviso that it is not porcine colostrum.

4. A composition according to claim 1, wherein the saturated fatty acids comprise at least one selected from the group consisting of butyric ($CH_3(CH_2)_2COOH$), lauric acid (dodecanoic acid; $CH_3(CH_2)_{10}COOH$), myristic acid (tetradecanoic acid; $CH_3(CH_2)_{12}COOH$), palmitic acid (hexadecanoic acid; $CH_3(CH_2)_{14}COOH$), stearic acid (octadecanoic acid, $CH_3(CH_2)_{16}COOH$), arachidic acid (eicosanoic acid; $CH_3(CH_2)_{18}COOH$).

5. A composition according to claim 1, wherein the mono-unsaturated fatty acids comprise at least one selected from the group consisting of palmitoleic acid ($CH_3(CH_2)_5CH=CH(CH_2)_7COOH$) and oleic acid ($CH_3(CH_2)_7CH=CH(CH_2)_7COOH$).

6. A composition according to claim 1, wherein the poly-unsaturated fatty acids comprise at least one selected from the group consisting of (alpha)-linolenic acid ($CH_3(CH_2CH=CH)_3(CH2)_7COOH$), linoleic acid ($CH_3(CH_2)_3(CH_2CH=CH)_2(CH_2)_7COOH$), arachidonic acid ($CH_3(CH_2)_3(CH_2CH=CH)_4(CH_2)_3COOH$), docosahexaenoic acid ($CH_3(CH_2CH=CH)_6(CH_2)_2COOH$) and eicosapentaenoic acid ($CH_3(CH_2CH=CH)_5(CH_2)_3COOH$).

7. A method of producing a composition according to claim 1 comprising mixing Ig and fatty acids.

8. A composition according claim 1, wherein said composition is a feed or fodder.

* * * * *